United States Patent
Delmas

(10) Patent No.: US 11,952,282 B2
(45) Date of Patent: Apr. 9, 2024

(54) METHOD FOR PRODUCING PURE AND HIGHLY CONCENTRATED CARBON DIOXIDE FROM A RENEWABLE LIGNOCELLULOSIC BIOMASS FEEDSTOCK

(71) Applicant: Société BIOEB, Auzeville-Tolosane (FR)

(72) Inventor: Michel Delmas, Auzeville-Tolosane (FR)

(73) Assignee: Société Bioeb, Auzeville-Tolosane (FR)

( * ) Notice: Subject to any disclaimer, the term of this patent is extended or adjusted under 35 U.S.C. 154(b) by 906 days.

(21) Appl. No.: 16/969,727

(22) PCT Filed: Feb. 15, 2019

(86) PCT No.: PCT/EP2019/053783
§ 371 (c)(1),
(2) Date: Aug. 13, 2020

(87) PCT Pub. No.: WO2019/158680
PCT Pub. Date: Aug. 22, 2019

(65) Prior Publication Data
US 2021/0002568 A1    Jan. 7, 2021

(30) Foreign Application Priority Data
Feb. 16, 2018 (EP) .................................. 18157086

(51) Int. Cl.
*C01B 32/50* (2017.01)
*C05D 7/00* (2006.01)
(Continued)

(52) U.S. Cl.
CPC ............... *C01B 32/50* (2017.08); *C05D 7/00* (2013.01); *C07C 1/12* (2013.01); *C07C 29/1518* (2013.01);
(Continued)

(58) Field of Classification Search
None
See application file for complete search history.

(56) References Cited

U.S. PATENT DOCUMENTS 9,108,894 B1 * 8/2015 Foody .................... C10L 1/023
2012/0202260 A1 8/2012 Maclachlan
(Continued)

FOREIGN PATENT DOCUMENTS

GB     2468483 A  *  9/2010  ................ C10L 1/00
WO  2011026243 A1     3/2011

OTHER PUBLICATIONS

International Search Report; priority document.
(Continued)

*Primary Examiner* — Wayne A Langel
(74) *Attorney, Agent, or Firm* — Greer, Burns & Crain, Ltd.

(57) ABSTRACT

A low energy production method for producing pure and highly concentrated carbon dioxide from a renewable lignocellulosic biomass feedstock comprising the steps of i) extracting lignins and hemicelluloses by putting a solid lignocellulosic raw material in the presence of a mixture of at least water and formic acid, at atmospheric pressure under conditions of temperature between 80° C. and 110° C., ii) fractionating, the primary solid fraction and the primary liquid fraction obtained at the end of the extraction step i), iii) separating the lignins from the intermediate liquid fraction, iv) producing a synthetic gas by feeding a gasification equipment with at least part of said primary solid fraction and/or at least part of said residual liquid fraction, and v) producing carbon dioxide and water by introducing dioxygen, or dioxygen enriched air, or air in said gasification equipment.

13 Claims, 2 Drawing Sheets

(51) Int. Cl.

| | |
|---|---|
| *C07C 1/12* | (2006.01) |
| *C07C 29/15* | (2006.01) |
| *C07C 29/151* | (2006.01) |
| *C07C 51/15* | (2006.01) |
| *C07G 1/00* | (2011.01) |
| *C08B 37/00* | (2006.01) |
| *C10J 3/72* | (2006.01) |
| *F02C 7/22* | (2006.01) |
| *F02C 6/02* | (2006.01) |

(52) U.S. Cl.
CPC .............. *C07C 51/15* (2013.01); *C07G 1/00* (2013.01); *C08B 37/0057* (2013.01); *C10J 3/72* (2013.01); *F02C 7/22* (2013.01); *C10J 2300/0916* (2013.01); *C10J 2300/092* (2013.01); *F02C 6/02* (2013.01)

(56) References Cited

U.S. PATENT DOCUMENTS

| | | | |
|---|---|---|---|
| 2013/0183733 A1 | 7/2013 | Delmas et al. | |
| 2016/0130369 A1* | 5/2016 | Iakovlev | C08B 15/08 435/99 |
| 2017/0002387 A1* | 1/2017 | Retsina | C12P 19/02 |
| 2018/0105475 A1* | 4/2018 | Keating | A01G 31/00 |

OTHER PUBLICATIONS

Özdencki et al., "A novel Biorefinery Integration Concept for Lignocellulosic Biomass" Energy Conversion and Management, vol. 149, Apr. 17, 2017, pp. 974-987.

Laosiripojana et al., "Fractionation of Lignin from Lignocellulosic Biomass and its Catalytic Depolymerization to Phenolic Monomers" PACCON 2017.

Li et al., "Sequential Two-Step Fractionation of Lignocellulose with Formic Acid Organosoly Followed by Alkaline Hydrogen Peroxide under Mild Conditions to Prepare Easily Saccharified Cellulose and Value-Added Lignin" Energy Conversion and Management, vol. 148, 2017, pp. 1426-1437.

Zhang et al., "Organosoly Pretreatment of Plant Biomass for Enhanced Enzymatic Saccharification" vol. 18, 2016, pp. 360-381.

De Wild, et al., "Organosoly Fractionation of Lignocellulosic Biomass for an Integrated Biorefinery" vol. 1, Feb. 2015, pp. 10-11.

Gu et al., "Life-Cycle GHG Emissions of Electricity from Syngas Prodoced by Pyrolyzing Woody Biomass" Proceedings of the 58th International Convention of Society of Wood Science and Technology, Jun. 2015, pp. 376-389.

Zeng, "New Bioproduction Systems for Chemivals and Fuels: Needs and New Development" Biotechnology Advances, vol. xxx, Jan. 11, 2019, pp. 1-11.

* cited by examiner

METHOD FOR PRODUCING PURE AND HIGHLY CONCENTRATED CARBON DIOXIDE FROM A RENEWABLE LIGNOCELLULOSIC BIOMASS FEEDSTOCK

CROSS-REFERENCES TO RELATED APPLICATIONS

This application claims the benefit of the International Application No. PCT/EP2019/053783, filed on Feb. 15, 2019, and of the European patent application No. 18157086.2 filed on Feb. 16, 2018, the entire disclosures of which are incorporated herein by way of reference.

FIELD OF THE INVENTION

The invention relates to a method for producing pure carbon dioxide from a renewable lignocellulosic biomass feedstock.

The invention more particularly relates to a method for producing pure and highly concentrated carbon dioxide from a renewable lignocellulosic biomass feedstock.

The invention also relates to a method for producing bioethanol, biofuels and biomolecules from the pure carbon dioxide.

BACKGROUND OF THE INVENTION

To date, and without considering the direct combustion of biomass, the main attempt to produce energy from plant biomass has been to produce biofuels such as bioethanol and other types of biofuels.

Fuels derived from plant biomass also emit carbon dioxide, but the carbon thus released was already present in the atmosphere.

Biofuels have thus appeared attractive from the point of view of carbon dioxide emissions.

In particular, the different technologies for the production of liquid biofuels—whether it is the transformation of lignocellulosic biomass by enzymatic hydrolysis or the thermochemical pathway—have low yields in terms of volume of production and in terms of energy balance.

The overall energy balance of ethanol production by the conventional biochemical pathway can be penalized by the necessary energy consumption associated with the cultivation of dedicated plants as well as by the energy consumption during the distillation operations.

In addition, in this sector, only the sugars contained in the plants are used for the production of biofuels and therefore for the production of energy.

Also, the costs of the enzymes do not permit the reaching of a sufficient economical balance—that is continually affected depending on the price of the crude oil.

In the thermochemical pathway, all the components of the biomass are used for production of the biofuels and the overall energy balance might be better, but the overall economic balance remains very low.

Thus, no solution has emerged for industrial mass production of biofuels that would be satisfactory with regards to the different energy, economic and global ecological balances.

Such a lignocellulosic vegetable raw material is, for example, available in mass when one considers the lignocellulosic residues in logging and in the production of palm or palm trees, or the production of rice straw and cereal straw at large, or the bagasse in the sugar industry. In these two cases, a very abundant raw material is available for carrying out the process according to the invention which, to date, finds no profitable industrial use and under environmentally acceptable conditions for the production of energy, and, for example, for the production "in situ" of electricity.

Biomass is the unique direct and renewable storage facility of solar energy, and lignocellulosic waste feedstock does represent a more or less important part of this renewable non-fossil power source.

Direct gasification of biomass is not a viable solution due to the very negative impact of lignins aromatic rings which induce the secondary formation of carbonaceous oils and residues without efficient known recovery.

Moreover, for various reasons, it has also become necessary in the polymer industry to move towards a progressive replacement of products derived from the petroleum industry (i.e., from petrochemicals) by products derived from biomass (green chemistry).

In such a context, it has been proposed in US-A1-2012/0202260 a process for concurrent recovery of lignins derivatives and synthetic gas (syngas) from a lignocellulosic feedstock according to a "Hybrid bio refining and gasification of lignocellulosic feedstocks". However, after separation of the lignins and gasification of the "solids streams" and of the "Semi-solid and solid wastes" to produce syngas using conventional gasification equipment, it is proposed in this document to process the syngas in order to produce various types of fuels such as Biodiesel, Butanol, Ethanol, Methanol, etc.

Syngas, or synthesis gas, is a fuel gas mixture consisting primarily of hydrogen (H2), carbon monoxide (CO), and very often some carbon dioxide (CO2).

Conversion of biomass to syngas is typically low-yield.

To date, no one has suggested or put forward the idea, that atmospheric carbon dioxide (CO2) can be an energy source and/or a promising raw material for the future, especially for replacing fossil oil.

Carbon dioxide (CO2) has become the focus of particular attention for major carbon dioxide producers.

Fossil carbon dioxide (CO2) is the major contributor to the greenhouse effect with its very damaging climatic consequences.

Theoretically, syngas is composed of equimolar amounts of hydrogen (H2) and carbon monoxide (CO) and carbon monoxide.

According to prior art techniques, the syngas obtained from gasification of lignocellulosic biomass is composed of impurities such as dust, tar(s), halogen and alkali compounds with inorganic impurities, being hydrogen sulfide (H2S), ammonium (NH3), hydrogen chloride (HCl), methane (CH4) and other light hydrocarbon, ethane (C2H6) contaminants of catalysts in downstream processes and specific cleaning operations processes are required to remove such contaminants.

A time consuming and very expensive gas (syngas) cleaning is thus required to remove contaminants and provide a syngas within specifications for downstream processes and syngas utilization, while a gas conditioning system is required to eliminate main gas compounds and adjust the H2/CO ratio.

The main steps here are reforming of hydrocarbons, CO-shift to adjust the H2/CO ratio and removal of carbon dioxide (CO2).

After such time consuming and expensive gas treatment by cleaning and conditioning, syngas obtained from lignocellulosic biomass is chemically similar (CO, H2) to syngas derived from fossil sources and can replace its fossil equivalent in all applications.

Thus, there is a global need for a global method operating in a closed cycle from atmospheric carbon dioxide ($CO_2$), thus without any contribution to the greenhouse effect and thus providing the first economic and ecological response to the necessary energy transition of the 21st century, based on lignocellulosic wastes or residues which, quantitatively and qualitatively on an annual basis, nowadays weigh about as much as oil and coal combined.

SUMMARY OF THE INVENTION

The invention proposes a low energy production method for producing carbon dioxide ($CO_2$) from a renewable lignocellulosic biomass feedstock (LRM) comprising the following steps:

i) extracting lignins and hemicelluloses by putting at least one solid lignocellulosic raw material in the presence of a mixture, composed of at least water and formic acid, at atmospheric pressure under controlled conditions of temperature between 80° C. and 110° C., with a dilution ratio of the at least one solid lignocellulosic raw material/liquid mixture comprised between 1 and 15, and for a determined period of time, depending on the nature of the at least one lignocellulosic raw material;

ii) fractionating, at atmospheric pressure, the primary solid fraction (PSF) and the primary liquid fraction (PLF) obtained at the end of the preceding extraction step i);

iii) separating the lignins from the intermediate liquid fraction (ILF), for example by precipitation by adding water, and obtaining a residual liquid fraction (RLF);

iv) producing a synthetic gas by feeding a gasification equipment with at least part of the primary solid fraction (PSF) and/or at least part of the residual liquid fraction (RLF);

v) producing carbon dioxide ($CO_2$) and water ($H_2O$) by introducing dioxygen ($O_2$), or dioxygen enriched air, or air in the gasification equipment.

According to other aspects of this method:

the step v) for producing carbon dioxide ($CO_2$) from the synthetic gas consists in introducing dioxygen ($O_2$), or dioxygen enriched air, or air in the gasification equipment for allowing the complete conversion of the cellulose ($C_6H_{10}O_5$) to synthetic gas, according to the formula $C_6H_{10}O_5 + \frac{1}{2}O_2 \rightarrow 6CO + 5H_2$;

the mixture used in the extraction step i) is composed only of water and of formic acid;

the mixture used in the extraction step i) is composed of at least water, formic acid and acetic acid in very small amounts, including at least acetic acid generated during the extraction step i);

the temperature is between 80° C. and 90° C., preferably equal to 85° C.;

during the extraction step i), the at least one solid lignocellulosic raw material is put in the presence of the mixture for a period of time comprised between 2 hours and 6 hours;

the carbon dioxide ($CO_2$) produced at step v) and or steam produced using the synthetic gas produced at step iv) are used as sources of energy in the the extraction, fractionation and/or separation steps i), ii) and/or iii);

The invention also proposes a method for producing industrial carbon dioxide-based products using the carbon dioxide ($CO_2$) obtained from the step v) of the method according to the invention, without cleaning or purifying said carbon dioxide ($CO_2$).

The industrial carbon dioxide-based products comprise bioethanol, biofuels, ethylene, formic acid.

The carbon dioxide-based biofuels and/or bioethanol are used as sources of energy in the the extraction, fractionation and/or separation steps i), ii) and/or iii).

The invention also proposes a method for horticultural or agricultural production in a greenhouse using the carbon dioxide fertilization effect using the carbon dioxide ($CO_2$) obtained from the step v) of the method according to the invention, without cleaning or purifying the carbon dioxide ($CO_2$).

BRIEF DESCRIPTION OF THE DRAWINGS

The present invention will be described in conjunction with reference to the attached drawings in which.

DETAILED DESCRIPTION OF THE PREFERRED EMBODIMENTS

All biomass contains cellulose, hemicelluloses and lignins in varying percentages, along with inorganic components which are the source of ash.

Cellulose is a straight-chain polymer comprising anhydroglucopyranose joined with ether bonds.

Hemicelluloses are a group of polysaccharides made up of various sugars.

Lignins is the most complex constituent and is a polymer structure of phenylpropane units.

The most prominent constituent of biomass is lignocellulose, which consists of the non-starch, fibrous part of plant material. Cellulose, hemicelluloses and lignins are the three main elements of lignocellulosic biomass. The cellulose-to-lignins ratio may vary and the proportion of cellulose and hemicelluloses are directly related to the gaseous products yield, while the lignins content determines the pyrolysis oil in the product.

It has been identified that cellulose, hemicelluloses and lignins fractions present in biomass feedstocks degrade at different temperature ranges during gasification. The variation in these constituents in biomass raw materials yields products with different calorific values. Gasification of pure cellulose does not yield water-soluble tars in the early stages.

This appears to be the consequence of the inhibition of the thermal polymerization by lignins during lignins/cellulose interactions in pyrolysis.

The rate of pyrolysis is thus directly related to cellulose fractions and inversely dependent upon lignins content in the feedstock.

Figure 1:
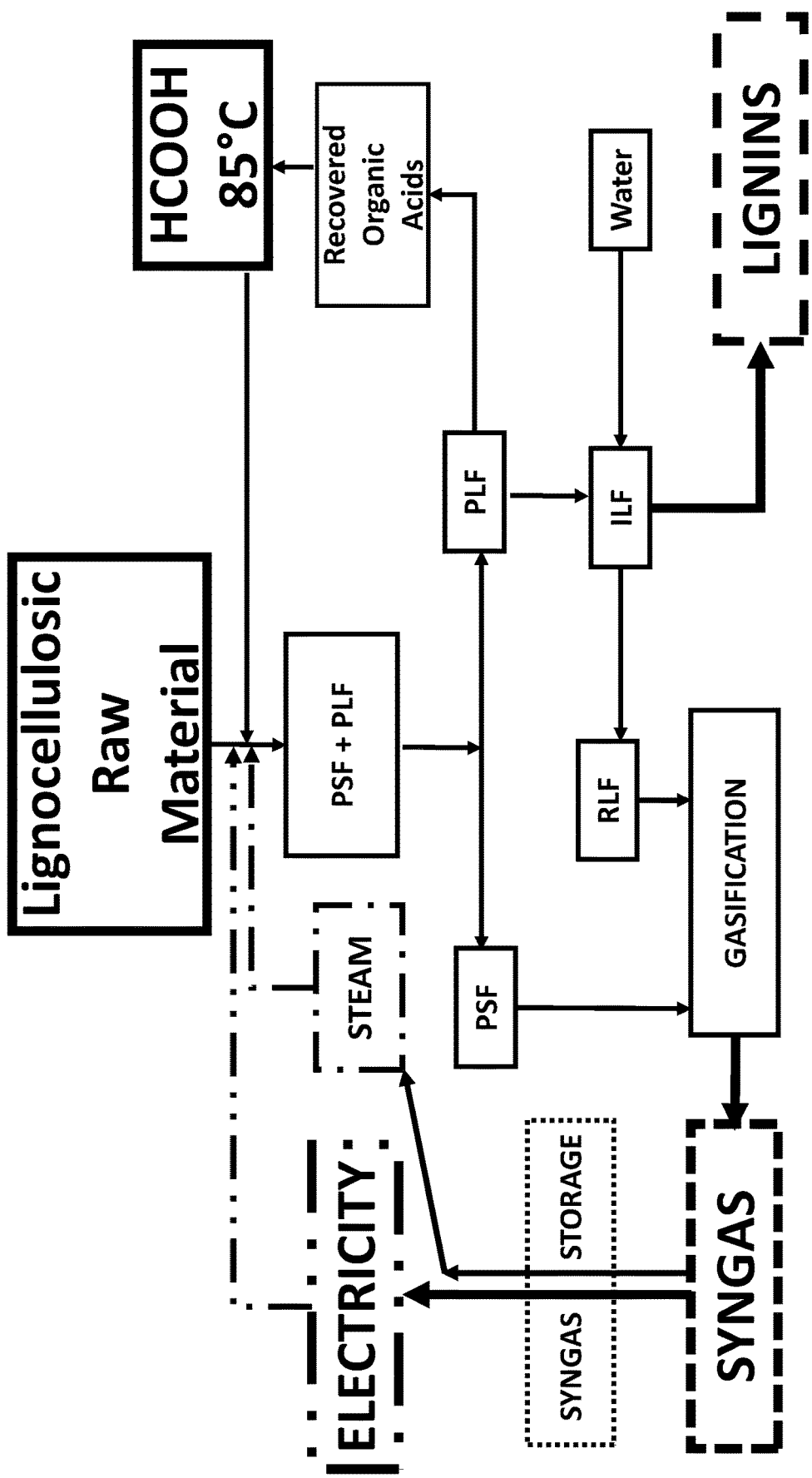
FIG. 1 schematically illustrates the main steps of an example of an acid based organosolv production process used for producing synthetic gas and energy from lignocellulosic raw material, possibly in an energetically autonomous way.
Figure 2:
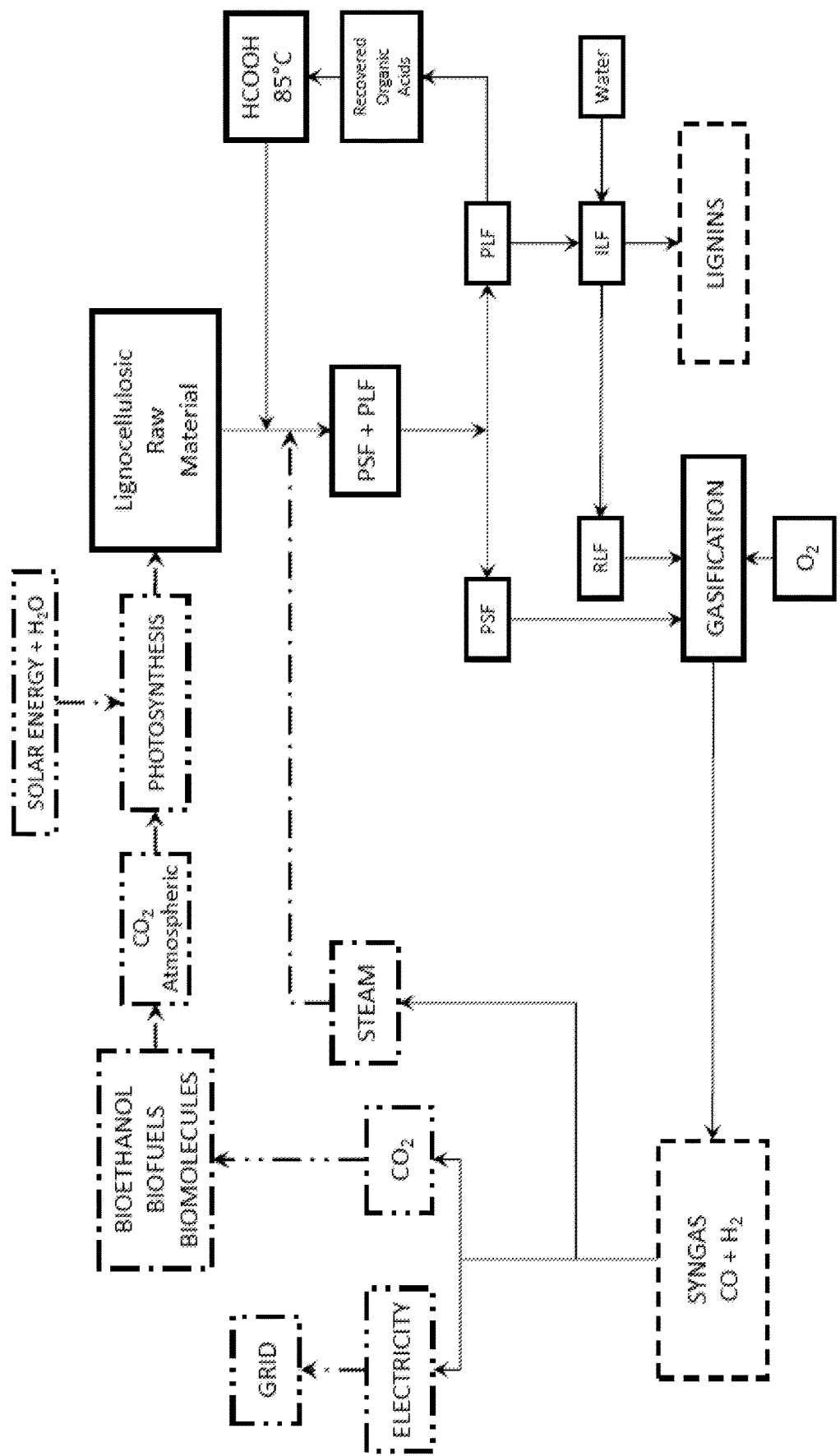
FIG. 2 schematically illustrates the main steps of a method according to the invention incorporating the process of FIG. 1 for producing synthetic gas, carbon dioxide, energy and industrial carbon dioxide-based products using the carbon dioxide ($CO_2$) produced from lignocellulosic raw material.

A first example of a process for the extraction of lignins from a biomass Lignocellulosic Raw Material (LRM) using a mixture of water ($H_2O$) and formic acid (HCOOH) at low temperature and atmospheric pressure, as illustrated at FIG. 1, is as follows.

The first step consisted in preparing a solution of formic acid in water using a ratio in weight of 85% of formic acid and 15% of water.

In a second step, 30 grams of a dried sample of lignocellulosic feedstock (LRM) and 270 grams of the liquid mixture of formic acid in water have been introduced in a 500 milliliters glass reactor.

The liquid/solid mass ratio (Dilution ratio) was thus for example equal to 9/1.

In order to increase the contact surface between liquid and solid, the lignocellulosic raw material sample can be crushed.

At the ambient/atmospheric pressure and using an oil bath, the mixture of the acid/water solution and of the biomass lignocellulosic raw material sample is heated at a temperature between 80° C.-90° C.

This mixture is thus stirred using a mechanical stirrer with an Inox anchor to have a homogenous temperature.

Using a thermometer, the temperature has been stabilized at 85° C.

This extraction step is a very low energy consuming step (working at a low temperature under 110° C.).

At the end of this period of time of reaction, the content of the reactor has been cooled to the ambient temperature and it contains a solid fraction and a liquid fraction.

The content has then been filtered to separate the raw solid cellulose (constituting the Primary Solid Fraction PSF in the sense of the invention) from the liquid phase of the content constituting a first portion P1 of the Primary Liquid Fraction PLF in the sense of the invention.

The separated cellulose has been washed with formic acid and then pressed and filtered to remove in a liquid form a second portion P2 of the primary liquid fraction PLF in the sense of the invention.

First portion P1 and second portion P2 have then been mixed together to obtain the Primary Liquid Fraction PLF.

This primary liquid fraction PLF has further been concentrated under vacuum, preferably with a heating thereof between 40° C.-50° C., at a pressure of 100 milliBar.

This concentration phase has been maintained until the moment where the dry matter content was about 50% to 60% in weight.

At this stage, all parts of the formic acid contained in the primary liquid fraction PLF are recovered and separated to obtain an Intermediate Liquid Fraction (ILF) in the sense of the invention.

It appears that some other organics acids, such as acetic acid (CH3-COOH) could be generated or produced during the extraction step starting with formic acid in very small amounts. These other acids, after recovery, are used in addition to the formic acid used for the above mentioned preparation of the water-acid mixture.

In order separate or "extract" the lignins from the hemicelluloses fraction in the Intermediate Liquid Fraction ILF, warm Water has been added to the Intermediate Liquid Fraction ILF for reaching a liquid/solid mass ratio, for example equal to 4/1.

With a view to enhancing the separation of the lignins from the hemicelluloses fraction, for example only, a high performance rotor/stator disperser has been used during a period of dispersion comprised between 2 and 3 minutes at a rotational speed greater than 15.000 revolutions per minute.

At the end of this dispersion step, it has been processed with a filtration step to separate the lignins from the hemicelluloses fraction and to obtain a Residual Liquid Fraction RLF in the sense of the invention.

The separated lignins have then been washed with warm water until a neutral pH of the filtrate has been reached.

The lignins have then been crushed and dried until reaching 94% of dry matter in weight, the drying temperature being not greater than 40° C.

At this stage the process has permitted to obtain:

A) non-oxidized, non-degraded and uncombined lignins with a controlled aliphatic hydroxyl content and controlled phenolic hydroxyl content; and B) a "compound" or mix comprising the Primary Solid Fraction PSF and the Residual Liquid Fraction RLF, that is available for direct gasification for production of syngas.

This compound of PSF+RLF available for gasification is ready for gasification in the sense that:
1) it does not contain any lignins, or in a much reduced proportion, that have been identified as an inhibitor of the gasification process;
2) the gasification process is conducted on a compound containing only sugars;
3) the sugars in the compound are in the most favorable H/C proportion for obtaining a synthetic gas or syngas having its optimal and maximum chemical and energetic efficiency, i.e., composed of equimolar amounts of carbon monoxide CO and of hydrogen H2;
4) syngas clean-up stages are no longer necessary, or are reduced to their minimum, as well as the problems inherent to the presence of ashes which are also avoided, or reduced when compared for instance with production process using syngas obtained by direct gasification of the biomass (Biomass Gasification) or of material obtained from starting lignocellulosic raw material, for example through known organosolv process, but containing lignins and/or hemicelluloses.

Concerning the "B) "compound" or mix comprising the Primary Solid Fraction PSF and the Residual Liquid Fraction RLF, that is available for direct gasification for production of syngas, the gasification is mainly or principally conducted using the Primary Solid Fraction PSF.

The Residual Liquid Fraction RLF—corresponding to the hemicelluloses—is relatively rich in protein (source of nitrogen) and also in minerals in the case of using cereal straw. The gasification of the Residual Liquid Fraction RLF from these raw materials could generate some NOx if it is mixed with the Primary Solid Fraction PSF.

The principles of gasification are as follows.

Gasification is a thermochemical process that converts a solid fuel (coal, wood, straw, etc.) into a gaseous fuel via the injection of a reduced and controlled quantity of an oxidizing agent (O2, air, CO2, water vapor . . . ).

It is therefore different from pyrolysis alone, which is a thermal operation carried out in the absence of an oxidizing agent, and from combustion, which is carried out in the abundant presence of an oxidizing agent.

According to general knowledge, gasification includes four main phases:
1) a drying phase integrated or not into the gasification reactor,
2) a pyrolysis phase which, under the effect of heat and in the absence of an oxidizing agent, produces volatile materials (CO, CO2, H2, CH4, H2Ovap and gaseous hydrocarbons called "tars") and coal,
3) a combustion phase, sometimes called partial oxidation, which by injection of an oxidizing agent (air, oxygen, water vapor) oxidizes the volatile matter or materials produced during the pyrolysis phase and sometimes part of the coal;

4) a gasification phase itself, also called reduction, which is closely linked to the combustion phase and which—through complex thermochemical reactions—converts coal (carbon) into a fuel gas rich in CO and H2 which is called "synthesis gas" or "syngas".

These four phases or steps of gasification are still present, but their spatial and temporal sequence and configuration may differ depending on the introduction mode, on the gasifying agent and on the reactor technology. These steps may take place in the same reactor or in separate chambers in the case of a tiered gasification.

PYROLYSIS: Pyrolysis consists in the decomposition of organic matter under the effect of heat in the absence of oxygen. Pyrolysis is also called carbonization, when the objective is the production of charcoal.

Under the effect of heating, between 300° C. and 700° C., volatile materials are formed—inside the particle—from hydrogen, oxygen and carbon present in the solid fuel, and are thereafter evacuated. The biomass is then transformed, on the one hand, into a solid part called "coke" (coal) and, on the other hand, into a gaseous part (pyrolysis gas). The volatile fraction consists of non-condensable gases (CO, H2, CO2, CH4, C2H6, C3H8, and C4H10) and of condensable gases (water, light and heavy tars). The solid fraction consists essentially of fixed carbon and of possible minerals and metals depending on the fuel used.

OXIDATION: The oxidation zone is the heart of a fixed bed gasifier.

First of all, the oxidation zone is the site of many chemical reactions, in particular those of combustion which provide:
the energy required for the other three phases or steps of the gasification,
gasifying agents (CO2 and H2Ovap), which react with coke during the reduction phase to form the synthesis gas or syngas.

In most of fixed-bed gasifiers, some of the coke in the area is oxidized with pyrolysis gases.

The choice of oxidant is fundamental to the design of the gasifier and depends on the end use of the gas. It is essentially the choice of oxidant that fixes the calorific value of the final gas at the outlet of the gasifier.

In practice, due to its ease of use, air is by far the most commonly used oxidant, particularly in the case of fixed-bed gas generators. Water vapor is sometimes used as an additive to improve the LCV (Lower Calorific Value) of the syngas.

The simple supply of air (78% N2 and 21% O2) as the oxidizing agent is to be avoided since it will bring nitrogen into the system and produce NOx. This is why it is preferable to use oxygen.

REDUCTION: In the reduction zone, pyrolysis coke is converted into gas ("coal gasification") through several competing chemical reactions.

Ideally, all pyrolysis gases are converted to carbon dioxide (CO2) and water vapor during partial oxidation. If oxygen is absent, then gasification can be summarized as only two endothermic heterogeneous reactions:

A) Water Vapor Gasification:

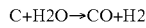

B) Carbon Dioxide Gasification (Boudouard Reaction)

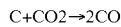

These two reactions are preponderant for synthesis gas production and they deserve special attention.

In addition, the gasification reaction of charcoal with carbon dioxide has a kinetics 2 to 5 times slower than the gasification reaction with water vapor.

Temperature has a very significant influence on the rate or speed of gasification. Indeed. This rate increases by a factor of 9 when the gasification temperature rises from 800 to 1000° C.

However not all pyrolysis gases reacted with oxygen during partial oxidation. Their presence increases the number of reactions in competition.

In view of the above mentioned characteristics of the compound for gasification according to the above described and illustrated process and of the characteristics and qualities of the synthetic gas obtained starting from this compound, for the efficient production of electricity, the synthetic gas obtained according to the process can be called "Electricity Efficient Syngas" or "Energy Efficient Syngas".

According to the invention, the method for producing pure carbon dioxide (CO2) through gasification requires the supply of pure oxygen (O2) to the gasifier or gasifying equipment.

This allows the complete conversion of cellulose (C6H10O5) to syngas (CO+H2) during gasification according to the formula:

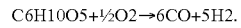

As illustrated in FIG. 1, before producing electricity or any other energy, such as steam for example, the syngas can be stored in a storage facility, preferably directly without any transformation or any addition, in order to safeguard its high efficiency properties for producing electricity.

The above process for producing synthetic gas can be industrially implemented using a batch technique for the extraction step i), also including stirring of the content of each batch.

This is advantageous when compared with diffusion techniques that imply long and energy consuming extraction periods.

This is also advantageous when compared with diffusion techniques that imply specific "calibration" preparation steps of the Lignocellulosic Raw Material (LRM) by cutting, crushing, micronizing, etc. depending on the plant waste used as raw material.

As illustrated at FIG. 1, the process can be designed as an energetically autonomous process by using electricity and/or any other energy (such as steam) produced in using the syngas as energy for producing the synthetic gas, and, for instance, during the extraction step using formic acid at 85° C.

The invention also permits the use of the syngas as a non-fossil power source for producing electricity, i.e., for producing electricity from renewable lignocellulosic biomass feedstocks in a power plant and according to a method for on-demand producing electricity from Non Fossil Power Sources (NFPS) and from a renewable lignocellulosic biomass feedstock (LRM).

This also permits on-demand continuously producing electricity from Non-Fossil Power Sources and from at least a lignocellulosic renewable biomass feedstock (LRM).

Such a method can be implemented in a factory or plant comprising at least:
a first facility for producing electricity using a Non Fossil Power Source NFPS; and
a second facility using Renewable Lignocellulosic Biomass Feedstock (LRM) for producing syngas obtained according to the above described process.

The renewable Non Fossil Power Source(s) is (are) to be chosen among Solar energy, Wind power, Wave power, Tidal power, Geothermal power and/or Hydropower.

Beyond the above listed advantages in using syngas obtained according to the above described process, the lignocellulosic raw material does appear as a "Backup fuel" or "Backup power source" for the production of electricity from Non Fossil Power Sources (NFPS) when such sources are not available or not sufficiently available.

This is, for instance, the case during the night for solar energy, when there is not sufficient wind, when the tide is out, when a hydroelectric dam is "empty", etc.

This fuel or power source is a backup solution in two ways.

Firstly, the renewable lignocellulosic raw material can be easily stored at the first facility.

Secondly, the synthetic gas or syngas can easily be stored in any appropriate storage facility and dispatched on demand to the electricity production means of the second facility.

The method according to the invention using renewable lignocellulosic biomass feedstock, and, in particular, wastes from agricultural production and from the forest industry, makes it possible to valorize a part of the components of the lignocellulosic biomass in the polymers industry, and the other components through the direct use of pure carbon dioxide ($CO_2$) and/or production of energy, for example production of electrical green or clean energy, with optimum energy, economic and ecological balances.

Pure carbon dioxide ($CO_2$) produced from cellulose has the characteristics of a raw material available at zero cost since it has until now been considered as emitted into the atmosphere from where it comes in its initial form and therefore without any impact.

Pure carbon dioxide ($CO_2$) can therefore be transformed on existing industrial bases, already known from the state of the art, into a considerable quantity of molecules of major industrial interest, therefore of perfectly biological origin (biomolecules), such as bioethanol, formic acid, ethylene, etc.

For example, many attempts are conducted for converting ethanol directly into butadiene which is the building "block" for about every major synthetic plastic or rubber.

Also, the pure carbon dioxide ($CO_2$) obtained according to the invention is highly concentrated when compared with the proportion of carbon dioxide ($CO_2$) present in the atmosphere.

When the bioethanol or a biofuel, obtained using carbon dioxide ($CO_2$) obtained according to the invention, is used through combustion, this combustion also produces a carbon dioxide ($CO_2$) which, if rejected in the atmosphere and in combination with water and the solar energy, is the basis for growing renewable lignocellulosic material.

This latter carbon dioxide ($CO_2$), or the carbon dioxide ($CO_2$) obtained according to the invention can be used in greenhouses for producing agricultural or horticultural consumable products, using the carbon dioxide fertilization effect.

The invention proposes a very efficient and cheap new method to concentrate carbon dioxide from the atmosphere using lignocellulosic biomass residues, built on the new use of pure cellulose as primary energetic compound, in opposition to all today's solutions which are very complex and expensive.

Due to the invention, carbon dioxide ($CO_2$) appears, as a perfect mediator for the direct use of solar energy on earth, without any greenhouse contribution, like solar cells of photosynthetic panels, with the decisive advantage to produce the same hydrocarbons as those coming from (fossil) oil.

The method according to the invention appears to be the first efficient process to replace fossil fuels by identical fuels but which are of atmospheric origin and no longer "fossil-sourced".

The invention is a totally new ecological, economical and realistic way to reduce the global warming on Earth.

While at least one exemplary embodiment of the present invention(s) is disclosed herein, it should be understood that modifications, substitutions and alternatives may be apparent to one of ordinary skill in the art and can be made without departing from the scope of this disclosure. This disclosure is intended to cover any adaptations or variations of the exemplary embodiment(s). In addition, in this disclosure, the terms "comprise" or "comprising" do not exclude other elements or steps, the terms "a" or "one" do not exclude a plural number, and the term "or" means either or both. Furthermore, characteristics or steps which have been described may also be used in combination with other characteristics or steps and in any order unless the disclosure or context suggests otherwise. This disclosure hereby incorporates by reference the complete disclosure of any patent or application from which it claims benefit or priority.

The invention claimed is:

1. A low energy production method for producing carbon dioxide from a renewable lignocellulosic biomass feedstock comprising the following steps:
   i) extracting lignins and hemicelluloses by putting at least one solid lignocellulosic raw material in a presence of a mixture, composed of at least water and formic acid, at atmospheric pressure under controlled conditions of temperature between 80° C. and 110° C., with a dilution ratio of said at least one solid lignocellulosic raw material/liquid mixture comprised between 1 and 15, and for a period of time, depending on a nature of the at least one lignocellulosic raw material;
   ii) fractionating, at atmospheric pressure, a primary solid fraction and a primary liquid fraction obtained at an end of the preceding extracting step i);
   iii) separating the lignins from an intermediate liquid fraction, and obtaining a residual liquid fraction;
   iv) producing a synthetic gas by feeding a gasification equipment with at least one of at least part of said primary solid fraction or at least part of said residual liquid fraction;
   v) producing carbon dioxide and water by introducing dioxygen, or dioxygen enriched air, or air in said gasification equipment.

2. The method according to claim 1 further comprising:
   producing industrial carbon dioxide-based products with the carbon dioxide obtained from said step v), without cleaning or purifying said carbon dioxide.

3. The method according to claim 2, wherein said industrial carbon dioxide-based products comprise bioethanol, biofuels, ethylene, formic acid.

4. The method according to claim 3, wherein said carbon dioxide-based products comprises biofuels or bioethanol, and wherein the method further comprises:
   producing energy for steps i), ii), iii) or, combinations thereof with the carbon dioxide-based products.

5. The method according to claim 1, wherein said temperature is between 80° C. and 90° C.

6. The method according to claim 5, wherein said temperature is equal to 85° C.

7. The method according to claim 1, wherein said step v) for producing carbon dioxide from said synthetic gas consists in introducing dioxygen, or dioxygen enriched air, or air in said gasification equipment for allowing a complete conversion of cellulose to synthetic gas.

8. The method according to claim 1, wherein said mixture used in said extracting step i) is composed only of water and of formic acid.

9. The method according to claim 1, wherein said mixture used in said extraction step i) is composed of at least water, formic acid and acetic acid in very small amounts, including at least acetic acid generated during the extracting step i).

10. The method according to claim 1, wherein, during said extraction step i), said at least one solid lignocellulosic raw material is put in the presence of said mixture for a period of time comprised between 2 hours and 6 hours.

11. The method according to claim 1, wherein the carbon dioxide produced at step v) and or steam produced using the synthetic gas produced at step iv) are used as sources of energy in at least one of said extracting, fractionating or separating steps i), ii) and/or iii.

12. The method of claim 1 further comprising:
providing the carbon dioxide obtained from said step v), without cleaning or purifying said carbon dioxide, to a greenhouse.

13. The method according to claim 1, wherein the separating in step iii) occurs by precipitation by adding water.

* * * * *